United States Patent [19]

Juto

[11] Patent Number: 5,666,957
[45] Date of Patent: Sep. 16, 1997

[54] METHOD AND DEVICE FOR RHINOSTEREOMETRIC MEASUREMENT

[76] Inventor: Jan-Erik Juto, Linnègatan 86, S-115 23 Stockholm, Sweden

[21] Appl. No.: 382,050

[22] PCT Filed: Aug. 12, 1993

[86] PCT No.: PCT/SE93/00670

§ 371 Date: Feb. 10, 1995

§ 102(e) Date: Feb. 10, 1995

[87] PCT Pub. No.: WO94/04077

PCT Pub. Date: Mar. 3, 1994

[30] Foreign Application Priority Data

Aug. 12, 1992 [SE] Sweden ................... 9202333

[51] Int. Cl.⁶ .................................................. A61B 6/00
[52] U.S. Cl. ........................ 128/665; 128/774; 606/130; 356/375
[58] Field of Search ............................ 128/664, 665, 128/653.1, 774; 606/130; 378/206; 356/375

[56] References Cited

U.S. PATENT DOCUMENTS

| | | | |
|---|---|---|---|
| 3,614,950 | 10/1971 | Rabey ................................... | 128/774 |
| 4,242,587 | 12/1980 | Lescrenier ........................... | 378/206 |
| 4,256,112 | 3/1981 | Kopf et al. ........................... | 606/130 |
| 4,294,544 | 10/1981 | Altschuler et al. | |
| 4,705,401 | 11/1987 | Addleman et al. | |
| 4,825,263 | 4/1989 | Desjardins et al. | |
| 5,143,076 | 9/1992 | Hardy et al. ........................... | 128/664 |

FOREIGN PATENT DOCUMENTS

| | | | |
|---|---|---|---|
| 3807578 | 9/1989 | Germany ................................ | 128/774 |
| 276623 | 3/1990 | Germany ................................ | 128/774 |
| 2006645 | 4/1992 | WIPO .................................... | 606/130 |

OTHER PUBLICATIONS

"Methods for Standardization of Nasal Mucosa Decongestion in Man", Jan–Erik Juto and Christer Lundberg, Rhinology 21, pp. 361–368, 1983.

Doctoral Thesis of Jan–Erik Juto, Rhinostereometry, Stockholm, Sweden, 1985.

Primary Examiner—Brian L. Casler
Attorney, Agent, or Firm—Burns, Doane, Swecker & Mathis, L.L.P.

[57] ABSTRACT

In rhinostereometric measurement, the positions in a fixed coordinate system are determined for a number of points on the nasal mucosa of a test subject. To obtain comparable results on different measuring occasions, the head of the test subject must occupy the same position in the coordinate system every time. By determining the position of a test subject's face in the coordinate system on every occasion of rhinostereometric measurement and transposing the measuring position of the face in the coordinate system to a reference position, the values of the points in the nose can be corrected for the displacement of the face from the reference position that has taken place since the last measurement, thereby to obtain comparable results that are always related to a reference position. Preferably, the position of the face in the coordinate system is determined by measuring the distance between fixed locations in the coordinate system and points in the test subject's face with the aid of distance-measuring lasers (8–12) mounted on a fixed frame (3) in the coordinate system. The displacement of the test subject's head is minimized by the mechanical fixing device (5) in the form of a spectacle frame. The measured values are processed in a computer (13).

18 Claims, 2 Drawing Sheets

METHOD AND DEVICE FOR RHINOSTEREOMETRIC MEASUREMENT

BACKGROUND AND SUMMARY

This invention relates to a method for rhinostereometric measurement as well as a device for implementing the method, comprising optical equipment for determining the coordinates of one or more points on a person's nasal mucosa.

Rhinostereometry is a known optical method used for measuring the congestion of the nasal mucosa. The head of the person to be subjected to such measuring is fixed in a coordinate system. The positions in the coordinate system of a number of points on the nasal mucosa are then determined with the aid of a surgical microscope placed on a micrometer table so as to be movable in all three dimensions. Rhinostereometry is described in more detail in a doctoral thesis by Jan-Erik Juto: Rhinostereometry, Stockholm, 1985, ISBN-91-7222-905-5.

In order that the results of rhinostereometric measurements should be comparable, the head of the test subject must occupy exactly the same position in the coordinate system every time. Positional accuracy has to be extremely high, since a point on the nasal mucosa moves about 4 mm at the most when the mucosa changes from a state of minimum congestion to one of maximum congestion. Such accuracy is hard to achieve.

The object of the invention is to provide a method and a device making it possible to obtain comparable results in rhinostereometric measurements performed on different occasions.

This object is achieved by a method having the distinctive features recited in appended claim 1 and by a device having the distinctive features recited in appended claim 6. Preferred embodiments of the invention are defined in the appended subclaims.

Because the position of a person's face in the coordinate system is determined on each measuring occasion and is then transposed to a reference position in the coordinate system, comparable results can be obtained on different measuring occasions regardless of the position of the face in the coordinate system by a corresponding transposition of the coordinates of the measured point on the nasal mucosa. In this way, the person's head need not be fixed in exactly the same position on all measuring occasions, but the head may change positions between them.

Preferably, the position of a person's face is determined by contactless distance measurement from fixed locations in the coordinate system, e.g. by means of radar, ultrasound or laser. At present, laser is preferred for reasons of accuracy. Also the coordinates of a point on the person's nasal mucosa are advantageously determined by laser instead of a surgical microscope.

To increase the accuracy of the positional determination, the movements of the person's head are advantageously restricted by mechanical fixing means, e.g. in the form of a spectacle frame.

BRIEF DESCRIPTION OF THE DRAWINGS

Preferred embodiments of the method and the device according to the invention will now be described in more detail with reference to the accompanying drawings.

DETAILED DESCRIPTION

Figure 1:
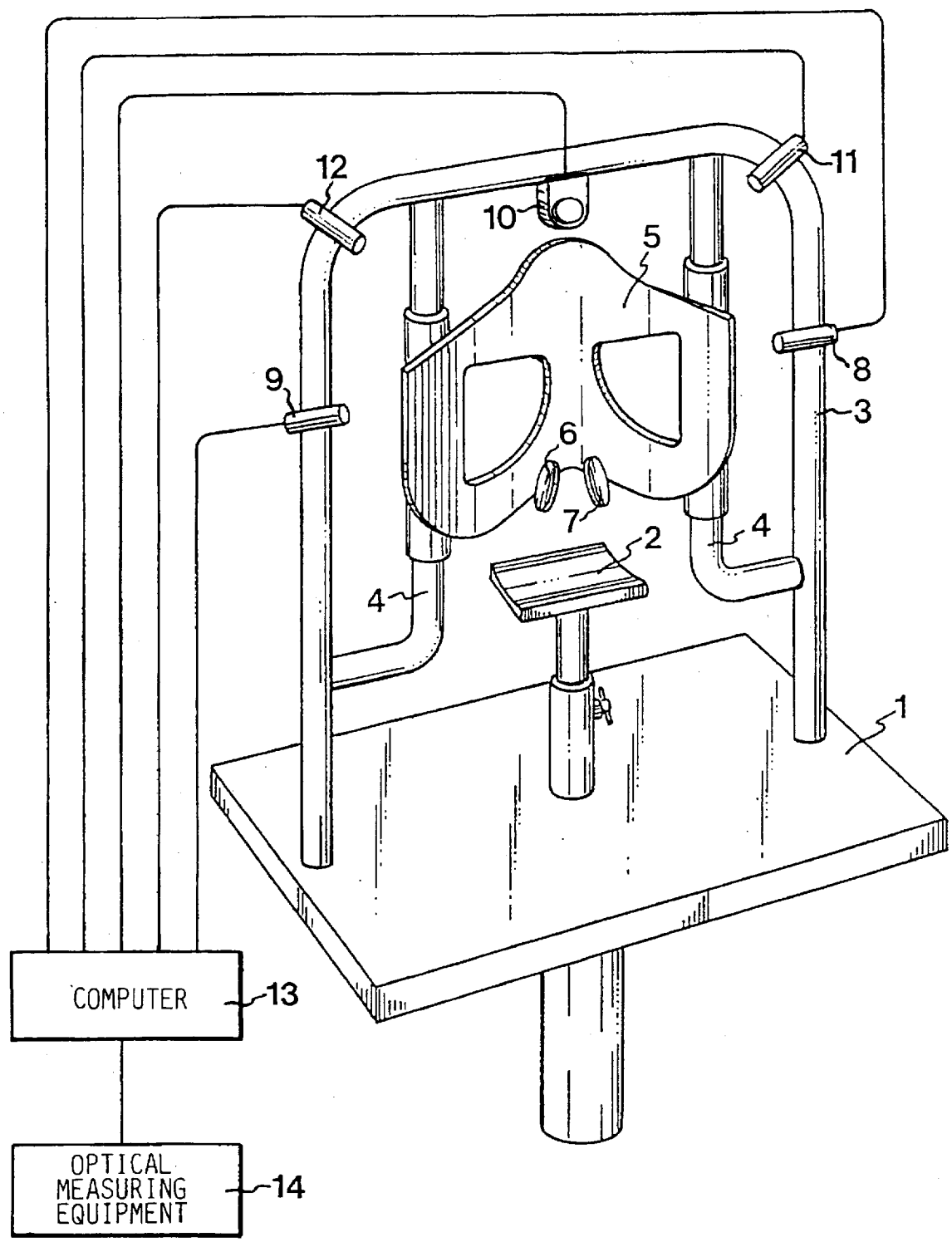
FIG. 1 shows an embodiment of the inventive device, some components being merely indicated schematically in the form of blocks.

The drawing illustrates a vertically adjustable table 1, on which are mounted a vertically adjustable chin rest 2 and a fixed frame 3. The frame 3 is provided with two fixed limbs 4 on which a spectacle frame 5 having two pad bridges 6, 7 is movably arranged. The spectacle frame serves as a means for fixing the head of the person to be subjected to rhinostereometry. Five distance-measuring lasers 8–12 are fixedly arranged on the frame 3 and so directed that the laser beams of two lasers 8, 9 impinge upon the test subject's face at the temples, that the laser beam of one laser 10 impinges upon the forehead, and that the laser beams of two lasers 11, 12 impinge upon the face on each side of the root of the nose. At present, such aiming of the lasers is believed to be the most suitable for determining the position of the head in a fixed coordinate system with maximum accuracy. Also, the lasers are advantageously directed towards the forehead, the temples and the root of the nose, since the skull here is close beneath the skin, making the shape of the face always essentially the same in these places. Naturally, the lasers should not be directed towards parts of the face that may swell owing to lack of sleep, heat or the like. The lasers are arranged at a distance of about 1–5 cm from the test subject's face. Use should, of course, be made of lasers providing a high resolution at such a distance. The lasers 8–12 are connected to a computer 13 which contains the software for determining, on the basis of the distances measured by the lasers, the coordinates in a fixed coordinate system of the points in the test subject's face on which the laser beams impinge. Furthermore, the inventive device includes optical measuring equipment 14 (shown merely in the form of a block) for determining the coordinates of the points on the nasal mucosa. The optical measuring equipment 14 may in known manner include a surgical microscope having an objective and an eyepiece so chosen as to give a shallow depth of field. The microscope can be so arranged on a micrometer table as to be movable along the x-, y- and z-axes in the fixed coordinate system in which are determined the coordinates of points in the face and on the nasal mucosa. In order to determine the coordinates of points on the nasal mucosa, it has to be possible to determine the position of the microscope on the micrometer table. As a hitherto unknown alternative, the optical measuring equipment may include a scanning distance-measuring laser which scans a predetermined surface or a predetermined distance. The optical equipment is connected to the computer 13, such that the position, when using a microscope, or the measured distance, when using a scanning laser, can be inputted into the computer 13.

The function of the device, as well as the method for rhinostereometric measurement, will be described below.

Figure 2:
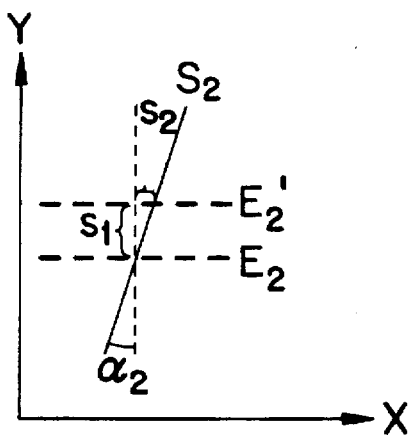
FIGS. 2 and 3 show different movements of curved surfaces oriented in three-dimensional coordinate systems.
Figure 3:
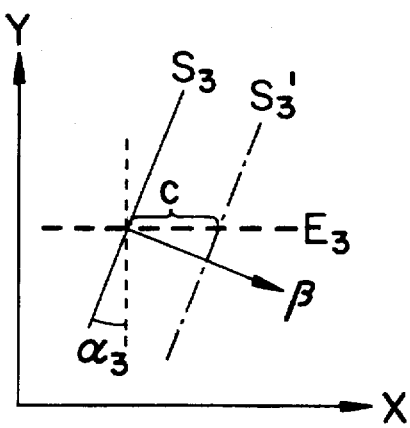

When a patient is to be subjected to rhinostereometric measurement for the first time, he is asked to put his chin on the chin rest 2, and the spectacle frame 5 is then moved downwards over his face so that the pad bridges 6 and 7 come to be applied against the root of the nose. Optionally, the spectacle frame 5 may be provided with a pressure transducer (not shown) emitting a signal when the spectacle frame is applied against the test subject's face by at least a predetermined pressure. This is conducive to increasing the accuracy, making it possible to always apply the spectacle frame against the face with the same pressure. When the test subject's face thus has been fixed so that only small movements are possible, the distance-measuring lasers 8–12 are activated. The microscope is displaced so as to focus a desired point on the nasal mucosa, i.e. placing it in the depth of field. When this is the case, measurement begins by the operator pushing a button, whereupon the position of the microscope on the micrometer table is read and inputted into the computer 13, and the distances, measured by the lasers 8–12, to the points towards which the lasers are directed are inputted into the computer 13. The computer converts the distances measured by the lasers 8–12 into coordinates in a fixed coordinate system and stores the coordinates in the computer memory as a set of reference coordinates. The computer 13 also calculates the coordinates of the point on the nasal mucosa for which the measurement has been performed. A more detailed description of how the coordinates of the point on the nasal mucosa are determined is found in the above-mentioned doctoral thesis. As stated in the doctoral thesis, a prerequisite for obtaining information regarding positional changes of a mucosal surface is accurate measurement of the distance from the surface to a reference point. The nasal cavity lacks a suitable reference point since the walls of the cavity are covered with a mucosa which varies in thickness. However, if the nose is placed in a three-dimensional, rectangular coordinate system, the origin of the coordinate system can be used as a reference point. As seen with reference to FIGS. 2–4, which show curved surfaces oriented in three-dimensional coordinate systems, the coordinates for an arbitrary point in a three-dimensional coordinate system can be determined by placing a measurement plane E at a right angle to the Y-axis and moving this plane along the axis until the point is identified in the plane (FIGS. 2–3). The intersection of the plane with the Y-axis gives the Y-coordinate for the point. The X and Z coordinates are obtained by reading off the position of the point along the X- and Z- axes, respectively.

Figure 4:
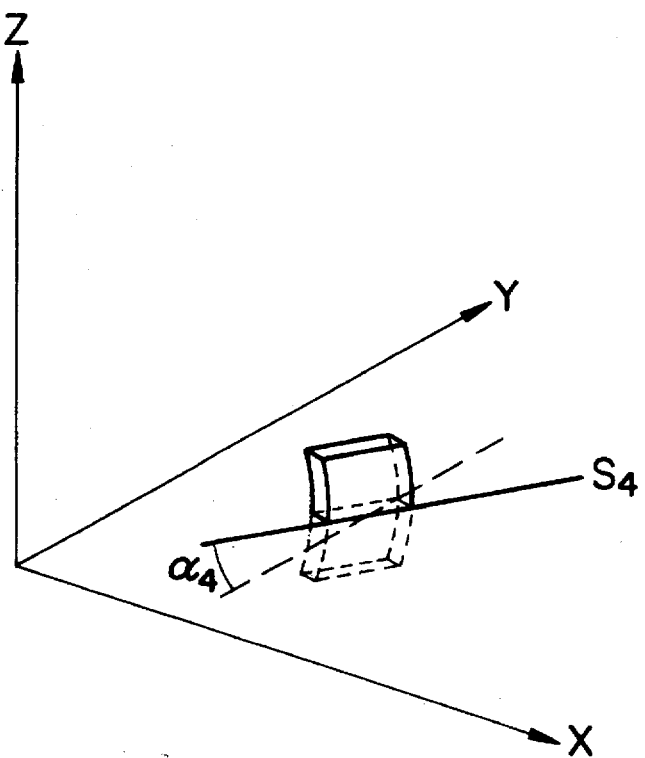
FIG. 4 shows a curved surface oriented in a three-dimensional coordinate system.

In FIGS. 2, 3, and 4, a curved surface is oriented in a three dimensional coordinate system in such a way that the surface cuts the XY-plane at right angles along the line of intersection $S_2$, $S_3$, and $S_4$, respectively, which line of intersection forms the angle $\alpha_2$, $\alpha_3$, $\alpha_4$, respectively. In FIG. 2, $S_2$ represents the line of intersection between the surface and the XY-plane. $\alpha_2$ is the angle between the $S_2$-line and the Y-axis. $E_2$ and $E_2'$ represent two positions at distance $s_1$ from each other of a plane perpendicular to the Y-axis and the XY-plane. $s_2$ represents the distance along the S-axis in the XY-plane between the line of intersection $S_2$ of the curved surface and the plane at position $E_2$ and $E_2'$. When the plane $E_2$ is moved for the distance $s_1$ along the Y-axis to the position $E_2'$ a new part of the surface is observed in the plane. This new position $E_2'$ is lateralized for the distance $s_2$. The angle $\alpha_2$ can then be calculated from $\tan\alpha_2 = s_1/s_2$.

In FIG. 3, $S_3$ represents the line of intersection between the surface and the XY-plane. $\alpha_3$ is the angle between the $S_3$-line and the Y-axis. $E_3$ represents the line of intersection between a plane perpendicular to the Y-axis and the XY-plane. $S_3$ and $S_3'$ represents two positions at distance c from each other along the X-axis of the line of intersections between the curved surface and the XY-plane as the curved surface moves in direction $\beta$ in the XY-plane. When the curved surface is moved in the direction $\beta$ in the XY-plane the intersection $S_3$ between the surface and the XY-plane moves to position $S_3'$, so that the part of the surface which is observed in the plane $E_3$ is moved a distance c. The true movement of the surface in direction $\beta$ can then be calculated when the angle $\alpha_3$ is known.

A measurement plane in a three-dimensional perpendicular coordinate system can be established using the plane of accurate focus of an optical system with a small depth of focus. If the optical system is movable in the coordinate system along its optical axis directed parallel to one of the axes of the coordinate system, it is possible to place the measurement plane in such a manner that an arbitrary point in the coordinate system can be identified in the plane. The coordinates for the point can then be determined.

A micrometer table, movable in all three right angular directions, is placed on a frame. Two of the three axes lie in the horizontal plane which also defines the direction of the third axis. The apparatus thus defines a three-dimensional perpendicular coordinate system.

A surgical microscope equipped with an objective and an ocular, selected to give a small depth of the focus, is placed on the micrometer table. The sharply delineated area in the coordinate system seen in the microscope represents the measurement plane E. The microscope is oriented in the coordinate system so that the plane of accurate focus is perpendicular to one of the horizontal axes. The ocular is equipped with a millimeter scale which is oriented parallel to the other horizontal axis in the system.

The nasal cavity is placed in the coordinate system when the volunteer to be examined bites down on an individually adapted tooth-splint fixed to the frame. To allow measurements of any visible surface inside the nose, the splint is fixed in a manner which allows the volunteer to be rotated in the horizontal plane.

When the next point on the nasal mucosa is to be measured, the test subject may have moved his head slightly in either direction so as to press harder against one pad bridge. Such movements of the head may, however, be compensated for by using the method and the device according to the invention. Owing to the lasers 8–12 measuring the distance to the points towards which they are directed when measuring on one point of the nasal mucosa, the computer 13 may calculate the coordinates of these points in the fixed coordinate system and thus determine the position occupied by the test subject's head when the most recent measurement in the nose was performed. By comparing the coordinates of the points in the face in the later measurement with the reference coordinates, the computer can determine how the coordinates of the point in the nose are to be corrected in order to compensate for the facial movements that have taken place. In practice, the coordinates of the points in the face from the later measurement can be transposed in the coordinate system so as to coincide with the reference coordinates, and the coordinates of the point in the nose be likewise transposed. Thus, the inventive method yields comparable results in different measurements also when the head does not occupy exactly the same position in the coordinate system on the different measuring occasions. The reference coordinates from the first measurement are stored and used in all subsequent measurements, so that the measured values can always be related to one another even when a long time has passed. Finally, it should be pointed out that the number of lasers as well as their positions may vary. Of course, higher accuracy can be achieved by using a larger number of lasers.

What is claimed is:

1. A method for rhinostereometric measurement, comprising the steps of:

determining a position of a face of a person in a coordinate system such that a reference position is defined;

determining coordinates of at least one point on a nasal mucosa of the person;

determining, simultaneously with the step of determining coordinates, the position of the face of the person in the coordinate system, such that a measuring position is defined;

transposing the measuring position in the coordinate system so as to coincide with the reference position in the coordinate system; and transposing the coordinates of the point on the nasal mucosa in the coordinate system in a manner corresponding to the manner in which the measuring position is transposed.

2. A method as set forth in claim 1, wherein the step of determining the position of the face of the person in the coordinate system includes measuring, without contacting the face of the person, a distance from a plurality of fixed locations in the coordinate system to a plurality of predetermined points in the face of the person, and determining the coordinates of these points in the coordinate system; and wherein the measuring position in the coordinate system is transposed so as to coincide with the reference position by transposing the coordinates of the plurality of points in the measuring position to the coordinates of the plurality of points in the reference position.

3. A method as set forth in claim 2, comprising the further step of measuring the distance between the plurality of points by laser.

4. A method as set forth in claim 2, wherein the plurality of points includes points on the forehead, at the temples and at the root of the nose of the person.

5. A method as set forth in claim 2, wherein the step of determining the coordinates of the point on the nasal mucosa includes measuring the distance to the point by laser.

6. A method as set forth in claim 1, comprising the further step of measuring a distance between the plurality of points by laser.

7. A method as set forth in claim 6, wherein the plurality of points includes points on the forehead, at the temples and at the root of the nose of the person.

8. A method as set forth in claim 6, wherein the step of determining the coordinates of the point on the nasal mucosa includes measuring the distance to the point by laser.

9. A method as set forth in claim 1, wherein the plurality of points includes points on the forehead, at the temples and at the root of the nose of the person.

10. A method as set forth in claim 9, wherein the step of determining the coordinates of the point on the nasal mucosa includes measuring a distance to the point by laser.

11. A method as set forth in claim 1, wherein the step of determining the coordinates of the point on the nasal mucosa includes measuring a distance to the point by laser.

12. A device for rhinostereometric measurement, comprising:

optical equipment for determining coordinates of one or more points on a person's nasal mucosa, a plurality of distance meters the distance meters being fixedly disposed in a coordinate system and each being adapted to measure a distance to a point in a face of a person to determine the coordinates of the point; and processing means for transposing the coordinates of each point of a plurality of points in the face of the person measured by the plurality of distance meters to a set of predetermined reference coordinates and for performing a corresponding transposition of coordinates of the one or more points on the nasal mucosa of the person.

13. A device as set forth in claim 12, wherein at least one of the distance meters is a distance-measuring laser.

14. A device as set forth in claim 13, wherein the optical equipment includes a distance-measuring laser.

15. A device as set forth in claim 13, further comprising means for mechanically fixing the head of the person in the coordinate system.

16. A device as set forth in claim 12, wherein the optical equipment includes a distance-measuring laser.

17. A device as set forth in claim 16, further comprising means for mechanically fixing the head of the person in the coordinate system.

18. A device as set forth in claim 12, further comprising means for mechanically fixing the head of the person in the coordinate system.

* * * * *